(12) United States Patent
Watterson (10) Patent No.: US 10,388,183 B2
(45) Date of Patent: Aug. 20, 2019

(54) ENCOURAGING ACHIEVEMENT OF HEALTH GOALS

(71) Applicant: ICON Health & Fitness, Inc., Logan, UT (US)

(72) Inventor: Scott R. Watterson, River Heights, UT (US)

(73) Assignee: ICON Health & Fitness, Inc., Logan, UT (US)

( * ) Notice: Subject to any disclaimer, the term of this patent is extended or adjusted under 35 U.S.C. 154(b) by 317 days.

(21) Appl. No.: 15/055,318

(22) Filed: Feb. 26, 2016

(65) Prior Publication Data

US 2016/0253918 A1    Sep. 1, 2016

Related U.S. Application Data

(60) Provisional application No. 62/126,272, filed on Feb. 27, 2015.

(51) Int. Cl.
| | |
|---|---|
| G09B 19/00 | (2006.01) |
| G09B 5/12 | (2006.01) |
| G16H 20/60 | (2018.01) |
| A63B 24/00 | (2006.01) |

(52) U.S. Cl.
CPC ......... *G09B 19/0092* (2013.01); *G09B 5/125* (2013.01); *G16H 20/60* (2018.01)

(58) Field of Classification Search
USPC .......................................................... 482/4
See application file for complete search history.

(56) References Cited

U.S. PATENT DOCUMENTS

| | | |
|---|---|---|
| 1,577,866 A | 3/1923 | Mossberg |
| 3,123,646 A | 3/1964 | Easton |
| 3,394,934 A | 7/1968 | Petros et al. |
| 3,579,339 A | 5/1971 | Chang et al. |
| 3,686,776 A | 8/1972 | Dahl |
| 3,903,613 A | 9/1975 | Bisberg |
| 4,023,795 A | 5/1977 | Pauls |

(Continued)

FOREIGN PATENT DOCUMENTS

| | | |
|---|---|---|
| BG | 2327612 | 2/1999 |
| EP | 1473219 | 11/2004 |

(Continued)

OTHER PUBLICATIONS

U.S. Appl. No, 61/593,290, filed Jan. 31, 2012, titled "System and Method to Promote Physical Exercise" (30 pages).

(Continued)

*Primary Examiner* — Masud Ahmed
(74) *Attorney, Agent, or Firm* — Maschoff Brennan (57) ABSTRACT

A method may include receiving a health goal of a user and receiving data describing a status of the user. The status of the user may be related at least in part to the health goal. The method may also include determining that the user has not achieved the health goal based at least in part on comparing the status of the user and the health goal. The method may further include sending an instruction to an environment-altering device associated with a location of the user. The instruction may be configured to generate an altered environment at the location. The altered environment may be configured to encourage the user toward achieving the health goal.

20 Claims, 2 Drawing Sheets

(56) References Cited

U.S. PATENT DOCUMENTS

| | | |
|---|---|---|
| 4,049,262 A | 9/1977 | Cunningham, Jr. |
| 4,300,760 A | 11/1981 | Bobroff |
| D286,311 S | 10/1986 | Martinell et al. |
| 4,681,318 A | 7/1987 | Lay |
| 4,684,126 A | 8/1987 | Dalebout et al. |
| 4,709,917 A | 12/1987 | Yang |
| 4,711,447 A | 12/1987 | Mansfield |
| 4,728,102 A | 3/1988 | Pauls |
| 4,750,736 A | 6/1988 | Watterson |
| 4,796,881 A | 1/1989 | Watterson |
| 4,813,667 A | 3/1989 | Watterson |
| 4,830,371 A | 5/1989 | Lay |
| 4,844,451 A | 7/1989 | Bersonnet et al. |
| 4,850,585 A | 7/1989 | Dalebout |
| D304,849 S | 11/1989 | Watterson |
| 4,880,225 A | 11/1989 | Lucas et al. |
| 4,883,272 A | 11/1989 | Lay |
| 4,887,967 A | 12/1989 | Letovsky et al. |
| 4,898,379 A | 2/1990 | Shiba |
| D306,468 S | 3/1990 | Watterson |
| D306,891 S | 3/1990 | Watterson |
| D307,614 S | 5/1990 | Bingham et al. |
| D307,615 S | 5/1990 | Bingham et al. |
| 4,921,242 A | 5/1990 | Watterson |
| 4,925,183 A | 5/1990 | Kim |
| 4,932,650 A | 6/1990 | Bingham et al. |
| 4,932,651 A | 6/1990 | Defaux |
| D309,167 S | 7/1990 | Griffin |
| D309,485 S | 7/1990 | Bingham et al. |
| 4,938,475 A | 7/1990 | Sargeant et al. |
| 4,938,478 A | 7/1990 | Lay |
| D310,253 S | 8/1990 | Bersonnet et al. |
| 4,955,599 A | 9/1990 | Bersonnet et al. |
| 4,971,316 A | 11/1990 | Dalebout et al. |
| D313,055 S | 12/1990 | Watterson |
| 4,974,832 A | 12/1990 | Dalebout |
| 4,979,737 A | 12/1990 | Kock |
| 4,981,294 A | 1/1991 | Dalebout et al. |
| D315,765 S | 3/1991 | Measom et al. |
| 4,998,725 A | 3/1991 | Watterson et al. |
| 5,000,442 A | 3/1991 | Dalebout et al. |
| 5,000,443 A | 3/1991 | Dalebout et al. |
| 5,000,444 A | 3/1991 | Dalebout et al. |
| D316,124 S | 4/1991 | Dalebout et al. |
| 5,013,033 A | 5/1991 | Watterson et al. |
| 5,014,980 A | 5/1991 | Bersonnet et al. |
| 5,016,871 A | 5/1991 | Dalebout et al. |
| D318,085 S | 7/1991 | Jacobson et al. |
| D318,086 S | 7/1991 | Bingham et al. |
| D318,699 S | 7/1991 | Jacobson et al. |
| 5,029,801 A | 7/1991 | Dalebout et al. |
| 5,034,576 A | 7/1991 | Dalebout et al. |
| 5,058,881 A | 10/1991 | Measom |
| 5,058,882 A | 10/1991 | Dalebout et al. |
| D321,388 S | 11/1991 | Dalebout |
| 5,062,626 A | 11/1991 | Dalebout et al. |
| 5,062,632 A | 11/1991 | Dalebout et al. |
| 5,067,710 A | 11/1991 | Watterson et al. |
| 5,072,929 A | 12/1991 | Peterson et al. |
| D323,009 S | 1/1992 | Dalebout et al. |
| D323,198 S | 1/1992 | Dalebout et al. |
| D323,199 S | 1/1992 | Dalebout et al. |
| D323,863 S | 2/1992 | Watterson |
| 5,088,729 A | 2/1992 | Dalebout |
| 5,090,694 A | 2/1992 | Pauls et al. |
| 5,102,380 A | 4/1992 | Jacobson et al. |
| 5,104,120 A | 4/1992 | Watterson et al. |
| 5,108,093 A | 4/1992 | Watterson |
| D326,491 S | 5/1992 | Dalebout |
| 5,122,105 A | 6/1992 | Engel et al. |
| 5,147,265 A | 9/1992 | Pauls et al. |
| 5,149,084 A | 9/1992 | Dalebout et al. |
| 5,171,196 A | 12/1992 | Lynch |
| D332,347 S | 1/1993 | Raadt et al. |
| 5,190,505 A | 3/1993 | Dalebout et al. |
| 5,195,937 A | 3/1993 | Engel et al. |
| 5,203,826 A | 4/1993 | Dalebout |
| D335,511 S | 5/1993 | Engel et al. |
| D335,905 S | 5/1993 | Cutter et al. |
| D336,498 S | 6/1993 | Engel et al. |
| 5,217,487 A | 6/1993 | Engel et al. |
| D337,361 S | 7/1993 | Engel et al. |
| D337,666 S | 7/1993 | Peterson et al. |
| D337,799 S | 7/1993 | Cutter et al. |
| 5,226,866 A | 7/1993 | Engel et al. |
| 5,240,417 A | 8/1993 | Smithson et al. |
| 5,244,446 A | 9/1993 | Engel et al. |
| 5,259,611 A | 11/1993 | Dalebout et al. |
| D342,106 S | 12/1993 | Campbell et al. |
| D344,112 S | 2/1994 | Smith |
| D344,557 S | 2/1994 | Ashby |
| 5,295,931 A | 3/1994 | Dreibelbis et al. |
| 5,302,161 A | 4/1994 | Loubert et al. |
| D347,251 S | 5/1994 | Dreibelbis et al. |
| D348,493 S | 7/1994 | Ashby |
| D348,494 S | 7/1994 | Ashby |
| 5,328,164 A | 7/1994 | Soga |
| D349,931 S | 8/1994 | Bostic et al. |
| 5,336,142 A | 8/1994 | Dalebout et al. |
| 5,344,376 A | 9/1994 | Bostic et al. |
| D351,202 S | 10/1994 | Bingham |
| D351,435 S | 10/1994 | Peterson et al. |
| D351,633 S | 10/1994 | Bingham |
| D352,534 S | 11/1994 | Dreibelbis et al. |
| 5,364,271 A | 11/1994 | Aknin et al. |
| D353,422 S | 12/1994 | Bostic et al. |
| 5,374,228 A | 12/1994 | Buisman et al. |
| 5,382,221 A | 1/1995 | Hsu et al. |
| 5,393,690 A | 2/1995 | Fu et al. |
| D356,128 S | 3/1995 | Smith et al. |
| 5,409,435 A | 4/1995 | Daniels |
| 5,429,563 A | 7/1995 | Engel et al. |
| 5,431,612 A | 7/1995 | Holden |
| 5,435,798 A | 7/1995 | Habing et al. |
| D360,915 S | 8/1995 | Bostic et al. |
| 5,456,648 A * | 10/1995 | Edinburg ........... A63B 22/0007 434/247 |
| 5,462,503 A | 10/1995 | Benjamin et al. |
| 5,489,249 A | 2/1996 | Brewer et al. |
| 5,492,517 A | 2/1996 | Bostic et al. |
| D367,689 S | 3/1996 | Wilkinson et al. |
| 5,511,740 A | 4/1996 | Loubert et al. |
| 5,512,025 A | 4/1996 | Dalebout et al. |
| D370,949 S | 6/1996 | Furner |
| D371,176 S | 6/1996 | Furner |
| 5,540,429 A | 7/1996 | Dalebout et al. |
| 5,549,533 A | 8/1996 | Olson et al. |
| 5,591,105 A | 1/1997 | Dalebout et al. |
| 5,591,106 A | 1/1997 | Dalebout et al. |
| 5,626,538 A | 5/1997 | Dalebout et al. |
| D380,024 S | 6/1997 | Novak et al. |
| 5,637,059 A | 6/1997 | Dalebout |
| D380,509 S | 7/1997 | Wilkinson et al. |
| 5,643,153 A | 7/1997 | Nylen et al. |
| 5,645,509 A | 7/1997 | Brewer et al. |
| D384,118 S | 9/1997 | Deblauw |
| 5,665,032 A | 9/1997 | Chen |
| 5,669,857 A | 9/1997 | Watterson et al. |
| 5,683,331 A | 11/1997 | Dalebout |
| D387,825 S | 12/1997 | Fleck et al. |
| 5,695,433 A | 12/1997 | Buisman |
| 5,720,200 A | 2/1998 | Anderson et al. |
| 5,720,698 A | 2/1998 | Dalebout et al. |
| D392,006 S | 3/1998 | Dalebout et al. |
| 5,762,584 A | 6/1998 | Daniels |
| 5,785,630 A | 7/1998 | Bobick et al. |
| 5,830,114 A | 11/1998 | Halfen et al. |
| 5,897,460 A | 4/1999 | McBride et al. |
| D412,953 S | 8/1999 | Armstrong |
| 5,938,571 A | 8/1999 | Stevens |
| D413,948 S | 9/1999 | Dalebout |
| 5,951,448 A | 9/1999 | Bolland |
| D416,596 S | 11/1999 | Armstrong |
| 6,003,166 A | 12/1999 | Hald et al. |

(56) References Cited

U.S. PATENT DOCUMENTS

| | | |
|---|---|---|
| D425,940 S | 5/2000 | Halfen et al. |
| 6,059,692 A | 5/2000 | Hickman |
| D428,949 S | 8/2000 | Simonson |
| 6,123,646 A | 9/2000 | Colassi |
| 6,171,217 B1 | 1/2001 | Cutler |
| 6,193,631 B1 | 2/2001 | Hickman |
| D450,872 S | 11/2001 | Dalebout et al. |
| 6,312,363 B1 | 11/2001 | Watterson et al. |
| D452,338 S | 12/2001 | Dalebout et al. |
| D453,543 S | 2/2002 | Cutler |
| D453,948 S | 2/2002 | Cutler |
| 6,413,191 B1 | 7/2002 | Harris et al. |
| 6,446,745 B1 | 9/2002 | Lee et al. |
| 6,447,424 B1 | 9/2002 | Ashby et al. |
| 6,454,679 B1 | 9/2002 | Radow |
| D463,948 S | 10/2002 | Innes |
| 6,458,060 B1 | 10/2002 | Watterson et al. |
| 6,563,225 B2 | 5/2003 | Soga et al. |
| 6,601,016 B1 | 7/2003 | Brown et al. |
| 6,626,799 B2 | 9/2003 | Watterson et al. |
| 6,695,581 B2 | 2/2004 | Wasson et al. |
| 6,701,271 B2 | 3/2004 | Spedale et al. |
| 6,702,719 B1 | 3/2004 | Brown et al. |
| 6,746,371 B1 | 6/2004 | Brown et al. |
| 6,749,537 B1 | 6/2004 | Hickman |
| 6,749,546 B2 | 6/2004 | Yang |
| 6,808,472 B1 | 10/2004 | Hickman |
| 6,863,641 B1 | 3/2005 | Brown et al. |
| 6,866,613 B1 | 3/2005 | Brown et al. |
| D507,311 S | 7/2005 | Butler et al. |
| 6,918,858 B2 | 7/2005 | Watterson et al. |
| 6,921,351 B1 | 7/2005 | Hickman et al. |
| 6,997,852 B2 | 2/2006 | Watterson et al. |
| D520,085 S | 5/2006 | Willardson et al. |
| 7,060,006 B1 | 6/2006 | Watterson et al. |
| 7,060,008 B2 | 6/2006 | Watterson et al. |
| 7,070,539 B2 | 7/2006 | Brown et al. |
| 7,097,588 B2 | 8/2006 | Watterson |
| D527,776 S | 9/2006 | Willardson et al. |
| 7,128,693 B2 | 10/2006 | Brown et al. |
| 7,166,062 B1 | 1/2007 | Watterson et al. |
| 7,166,064 B2 | 1/2007 | Watterson et al. |
| 7,303,510 B2 | 12/2007 | Gebhardt |
| 7,455,622 B2 | 11/2008 | Watterson et al. |
| 7,491,154 B2 | 2/2009 | Yonehana et al. |
| D588,655 S | 3/2009 | Utykanski |
| 7,510,509 B2 | 3/2009 | Hickman |
| 7,537,546 B2 | 5/2009 | Watterson et al. |
| 7,549,947 B2 | 6/2009 | Hickman et al. |
| 7,556,590 B2 | 7/2009 | Watterson et al. |
| 7,575,536 B1 | 8/2009 | Hickman |
| D604,373 S | 11/2009 | Dalebout et al. |
| 7,625,315 B2 | 12/2009 | Hickman |
| 7,628,730 B1 | 12/2009 | Watterson et al. |
| 7,637,847 B1 | 12/2009 | Hickman |
| 7,645,212 B2 | 1/2010 | Ashby et al. |
| 7,645,213 B2 | 1/2010 | Watterson |
| 7,648,446 B2 | 1/2010 | Chiles et al. |
| 7,713,171 B1 | 5/2010 | Hickman |
| 7,789,800 B1 | 9/2010 | Watterson et al. |
| 7,837,595 B2 | 11/2010 | Rice |
| 7,841,964 B2 | 11/2010 | Radow |
| 7,857,731 B2 | 12/2010 | Hickman et al. |
| 7,862,476 B2 | 1/2011 | Blau et al. |
| 7,862,478 B2 | 1/2011 | Watterson et al. |
| D635,207 S | 3/2011 | Dalebout et al. |
| 7,980,996 B2 | 7/2011 | Hickman |
| 7,981,000 B2 | 7/2011 | Watterson et al. |
| 7,985,164 B2 | 7/2011 | Ashby |
| 8,029,415 B2 | 10/2011 | Ashby et al. |
| D650,451 S | 12/2011 | Olson et al. |
| D652,877 S | 1/2012 | Dalebout et al. |
| 8,128,533 B2 | 3/2012 | Nakagawa et al. |
| D659,775 S | 5/2012 | Olson et al. |
| D659,777 S | 5/2012 | Watterson et al. |
| D660,383 S | 5/2012 | Watterson et al. |
| D664,613 S | 7/2012 | Dalebout et al. |
| 8,251,874 B2 | 8/2012 | Ashby et al. |
| 8,298,123 B2 | 10/2012 | Hickman |
| D671,177 S | 11/2012 | Sip |
| D671,178 S | 11/2012 | Sip |
| D673,626 S | 1/2013 | Olson et al. |
| 8,690,735 B2 | 4/2014 | Watterson et al. |
| D707,763 S | 6/2014 | Cutler |
| 8,758,201 B2 | 6/2014 | Ashby et al. |
| 8,784,270 B2 | 7/2014 | Watterson |
| D712,493 S | 9/2014 | Ercanbrack et al. |
| 8,845,493 B2 | 9/2014 | Watterson et al. |
| 8,911,330 B2 | 12/2014 | Watterson et al. |
| 8,954,290 B2 * | 2/2015 | Yuen ..................... G06F 3/011 702/160 |
| 8,986,165 B2 | 3/2015 | Ashby |
| 8,992,387 B2 | 3/2015 | Watterson et al. |
| D726,476 S | 4/2015 | Ercanbrack |
| 9,028,368 B2 | 5/2015 | Ashby et al. |
| 9,028,370 B2 | 5/2015 | Watterson et al. |
| D731,011 S | 6/2015 | Buchanan |
| 9,119,983 B2 | 9/2015 | Rhea |
| 9,123,317 B2 | 9/2015 | Watterson et al. |
| 9,142,139 B2 | 9/2015 | Watterson et al. |
| 9,149,683 B2 | 9/2015 | Smith |
| 9,186,549 B2 | 11/2015 | Watterson et al. |
| 9,241,635 B2 * | 1/2016 | Yuen ................. A61B 5/02405 |
| 9,254,416 B2 | 2/2016 | Ashby |
| 9,339,691 B2 | 5/2016 | Brammer |
| 9,460,632 B2 | 10/2016 | Watterson |
| 9,463,356 B2 | 10/2016 | Rhea |
| 9,586,090 B2 | 3/2017 | Watterson et al. |
| 9,586,091 B2 | 3/2017 | Reich et al. |
| 9,636,567 B2 | 5/2017 | Brammer et al. |
| 9,878,210 B2 | 1/2018 | Watterson |
| 9,943,722 B2 | 4/2018 | Dalebout |
| D826,350 S | 8/2018 | Hochstrasser |
| D827,733 S | 9/2018 | Hochstrasser |
| 10,065,064 B2 | 9/2018 | Smith et al. |
| 10,071,285 B2 | 9/2018 | Smith et al. |
| 10,085,586 B2 | 10/2018 | Smith et al. |
| 10,136,842 B2 | 11/2018 | Ashby |
| 10,186,161 B2 | 1/2019 | Watterson |
| 10,220,259 B2 | 3/2019 | Brammer |
| 10,226,664 B2 | 3/2019 | Dalebout |
| 10,252,109 B2 | 4/2019 | Watterson |
| 10,272,317 B2 | 4/2019 | Watterson |
| 2001/0027266 A1 * | 10/2001 | Hautala ................. A61B 5/222 600/16 |
| 2002/0016235 A1 | 2/2002 | Ashby et al. |
| 2002/0077221 A1 | 6/2002 | Dalebout et al. |
| 2002/0159253 A1 | 10/2002 | Dalebout et al. |
| 2004/0091307 A1 | 5/2004 | James |
| 2004/0171464 A1 | 9/2004 | Ashby et al. |
| 2004/0171465 A1 | 9/2004 | Hald et al. |
| 2005/0049123 A1 | 3/2005 | Dalebout et al. |
| 2005/0077805 A1 | 4/2005 | Dalebout et al. |
| 2005/0107229 A1 | 5/2005 | Wickens |
| 2005/0164832 A1 * | 7/2005 | Maschke ............ A63B 69/0028 482/8 |
| 2005/0164839 A1 | 7/2005 | Watterson et al. |
| 2005/0272577 A1 | 12/2005 | Olson et al. |
| 2007/0117683 A1 | 5/2007 | Ercanbrack et al. |
| 2007/0142175 A1 | 6/2007 | Morgan et al. |
| 2007/0254778 A1 | 11/2007 | Ashby |
| 2008/0051256 A1 | 2/2008 | Ashby et al. |
| 2008/0242520 A1 | 10/2008 | Hubbard |
| 2008/0300110 A1 | 12/2008 | Smith et al. |
| 2009/0105052 A1 | 4/2009 | Dalebout et al. |
| 2009/0181826 A1 | 7/2009 | Turner et al. |
| 2011/0009240 A1 | 1/2011 | Chiu et al. |
| 2012/0071301 A1 | 3/2012 | Kaylor et al. |
| 2012/0237911 A1 | 9/2012 | Watterson |
| 2013/0095978 A1 | 4/2013 | Sauter |
| 2013/0165195 A1 | 6/2013 | Watterson |
| 2013/0172152 A1 | 7/2013 | Watterson |
| 2013/0172153 A1 | 7/2013 | Watterson |
| 2013/0178334 A1 | 7/2013 | Brammer |

(56) References Cited

U.S. PATENT DOCUMENTS

| | | |
|---|---|---|
| 2013/0196298 A1 | 8/2013 | Watterson |
| 2013/0196821 A1 | 8/2013 | Watterson et al. |
| 2013/0196822 A1 | 8/2013 | Watterson et al. |
| 2013/0218585 A1 | 8/2013 | Watterson |
| 2013/0267383 A1 | 10/2013 | Watterson |
| 2013/0268101 A1 | 10/2013 | Brammer |
| 2013/0274067 A1 | 10/2013 | Watterson et al. |
| 2014/0073970 A1 | 3/2014 | Ashby |
| 2014/0121071 A1 | 5/2014 | Strom et al. |
| 2014/0135173 A1 | 5/2014 | Watterson |
| 2014/0194260 A1 | 7/2014 | Campanaro et al. |
| 2014/0287884 A1 | 9/2014 | Buchanan |
| 2014/0309085 A1 | 10/2014 | Watterson et al. |
| 2015/0141202 A1 | 5/2015 | Ellis et al. |
| 2015/0238817 A1 | 8/2015 | Watterson |
| 2015/0250418 A1 | 9/2015 | Ashby |
| 2015/0251055 A1 | 9/2015 | Ashby |
| 2015/0253210 A1 | 9/2015 | Ashby et al. |
| 2015/0253735 A1 | 9/2015 | Watterson |
| 2015/0253736 A1 | 9/2015 | Watterson |
| 2015/0258560 A1 | 9/2015 | Ashby |
| 2015/0327804 A1* | 11/2015 | Lefever ............... A61B 5/0205 600/483 |
| 2016/0063615 A1 | 3/2016 | Watterson |
| 2016/0092909 A1 | 3/2016 | Watterson |
| 2016/0107065 A1 | 4/2016 | Brammer |
| 2016/0121074 A1 | 5/2016 | Ashby |
| 2016/0148535 A1 | 5/2016 | Ashby |
| 2016/0148536 A1 | 5/2016 | Ashby |
| 2016/0250519 A1 | 9/2016 | Watterson |
| 2016/0253918 A1 | 9/2016 | Watterson |
| 2017/0011210 A1* | 1/2017 | Cheong ............... H04W 12/06 |
| 2017/0193578 A1 | 7/2017 | Watterson |
| 2017/0266503 A1 | 9/2017 | Watterson et al. |
| 2017/0266532 A1 | 9/2017 | Watterson |
| 2017/0266533 A1 | 9/2017 | Dalebout |
| 2017/0270820 A1 | 9/2017 | Ashby |
| 2018/0084817 A1 | 3/2018 | Capell et al. |
| 2018/0085630 A1 | 3/2018 | Capell et al. |
| 2018/0089396 A1 | 3/2018 | Capell et al. |
| 2018/0099116 A1 | 4/2018 | Ashby |
| 2018/0111034 A1 | 4/2018 | Watterson |
| 2019/0080624 A1 | 3/2019 | Watterson |

FOREIGN PATENT DOCUMENTS

| | | |
|---|---|---|
| EP | 2338782 | 6/2011 |
| EP | 2352667 A1 | 8/2011 |
| EP | 2657865 | 10/2013 |
| JP | 20022344179 | 8/2002 |
| JP | 2003180899 | 7/2003 |
| WO | 2015154046 | 10/2015 |

OTHER PUBLICATIONS

U.S. Appl. No. 62/126,272, filed Feb. 27, 2015, titled "Encouraging Achievement of Health Goals" (33 pages).

European Search Report issued in European Application No. 15196354.3 dated Apr. 8, 2016, 9 pages.

* cited by examiner

ENCOURAGING ACHIEVEMENT OF HEALTH GOALS

CROSS-REFERENCE TO RELATED APPLICATIONS

This patent application claims the benefit of and priority to U.S. Provisional Application No. 62/126,272, filed Feb. 27, 2015.

BACKGROUND

Field

Embodiments discussed herein generally relate to encouraging achievement of health goals. In particular, some embodiments may relate to altering an environment of a user's location to encourage the user toward achieving a health goal.

Relevant Technology

Exercising and eating healthy on a consistent and ongoing basis are common challenges for many people. Studies suggest that human heuristics and biases may introduce challenges to successfully implementing an exercise routine and/or eating healthy.

Research indicates that humans may operate under a time-inconsistent model of discounting described as hyperbolic discounting. For example, given two similar rewards, humans show a preference for a reward that arrives sooner over a reward that arrives later. In the context of health and fitness, people may discount the effort needed to perform tasks in the future, potentially leading people to make health-conscious plans for their future selves. Research also indicates that humans may assign more importance to immediate wants than to long-term wants, often described as present bias or immediacy effect. For example, a person may be driven to satisfy immediate wants even where those immediate wants are inconsistent with their long-term wants. Thus, notwithstanding their plans to exercise and to eat healthy meals, people may give in to more immediate wants and may choose not to exercise and/or may eat less healthy meals when it comes time to actually exercise and/or to eat.

Studies of hyperbolic discounting and present bias may confirm what people have long known, that making plans to exercise and to eat healthy is often much easier than actually exercising and eating healthy.

Many motivational tools exist to help people execute their well-intentioned health plans. However, many of the motivational tools are often ineffective for some people.

The subject matter claimed herein is not limited to embodiments that solve any disadvantages or that operate only in environments such as those described above. Rather, this background is only provided to illustrate one exemplary technology area where some embodiments described herein may be practiced.

SUMMARY

Embodiments may relate to systems, methods, and devices for encouraging users to achieve health goals. A user's progress toward achieving a defined health goal may be considered. If the user has not achieved their health goal, one or more environment-altering devices at the user's location may be instructed to alter the environment of the location for encouraging the user to achieve their health goal. The altered environment may be negated when the user begins actively working toward the health goal and/or successfully achieves the health goal.

The health goal and/or the parameters for altering the environment may be set by the user in advance, when the user's propensity for hyperbolic discounting may lead the user to set parameters to create an altered environment that will effectively encourage the user to achieve their health goal.

In some instances, the altered environment may be temporarily negated by the user through performing a complex, time-consuming, or otherwise unenjoyable task. The user may thus be discouraged from impulsively overriding the altered environment instead of working toward achieving the health goal. In some other instances, the health goals may be temporarily suspended in advance without inconveniencing the user, as the user's choices for their future may be less impulsive.

This Summary introduces a selection of concepts in a simplified form that are further described below in the Detailed Description. This Summary is not intended to identify key features or essential characteristics of the claimed subject matter, nor is it intended to be used as an aid in determining the scope of the claimed subject matter.

In an aspect of the disclosure, a method may include receiving a health goal of a user and receiving data describing a status of the user. The status of the user may be related at least in part to the health goal. The method may also include determining that the user has not achieved the health goal based at least in part on comparing the status of the user and the health goal. The method may further include sending an instruction to an environment-altering device associated with a location of the user. The instruction may be configured to generate an altered environment at the location. The altered environment may be configured to encourage the user toward achieving the health goal.

Another aspect of the disclosure may include any combination of the above-mentioned features and the method may further include receiving data describing an updated status of the user after sending the instruction to the environment-altering device. Updated instructions may be sent to the environment-altering device associated with the location of the user. The updated instruction may be configured to generate an updated environment at the location.

Yet another aspect of the disclosure may include any combination of the above-mentioned features and the method may further include determining that the user is actively working toward achieving the health goal based at least in part on the comparison of the updated status of the user and the health goal. The updated environment may be configured to negate the altered environment.

Still yet another aspect of the disclosure may include any combination of the above-mentioned features and the method may further include determining that the user is not actively working toward achieving the health goal based at least in part on the comparison of the updated status of the user and the health goal. The updated environment may be configured to further encourage the user toward achieving the health goal.

A further aspect of the disclosure may include any combination of the above-mentioned features and the method may further include determining that the user has achieved the health goal based at least in part on the comparison of the updated status of the user and the health goal. The updated environment may be configured to negate the altered environment.

Yet another further aspect of the disclosure may include any combination of the above-mentioned features and the method may further include determining that the user is projected to achieve the health goal based at least in part on the comparison of the updated status of the user and the health goal. The updated environment may be configured to negate the altered environment.

Another aspect of the disclosure may include any combination of the above-mentioned features and the method may further include determining that the user is not projected to achieve the health goal based at least in part on comparing the status of the user and the health goal.

Yet another aspect of the disclosure may include any combination of the above-mentioned features and the method may further include receiving an operating parameter from the user. The altered environment may further be based at least in part on the operating parameter.

Still yet another aspect of the disclosure may include any combination of the above-mentioned features and the altered environment may be associated with a change in a temperature of the location.

A further aspect of the disclosure may include any combination of the above-mentioned features and the altered environment may be associated with blocked access to a network location.

Yet another further aspect of the disclosure may include any combination of the above-mentioned features and the altered environment may be associated with a change in lighting of the location.

Still yet another further aspect of the disclosure may include any combination of the above-mentioned features and the altered environment may be associated with blocked access to a device located at the location.

A further aspect of the disclosure may include any combination of the above-mentioned features and the data describing a status of the user may be received by way of one or more of a wearable fitness-tracking device, an exercise device, a smartwatch, and a smartphone.

Additional features and advantages will be set forth in the description which follows, and in part will be obvious from the description, or may be learned by the practice of the embodiments. The features and advantages of the embodiments will be realized and obtained by means of the instruments and combinations particularly pointed out in the claims. These and other features will become more fully apparent from the following description and claims, or may be learned by the practice of the embodiments as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DESCRIPTION OF EMBODIMENTS

Embodiments may relate to systems, methods, and devices for encouraging users to achieve health goals. The embodiments may exploit the same human heuristics and biases that may make executing health plans a challenge to encourage a user to execute the health plans. Although described in the context of health plans such as exercise plans, nutrition plans and the like, the embodiments are not limited to health and fitness, but may generally be used to encourage a user to execute a plan that the user's impulsive tendencies may derail. By way of example, the embodiments may be used to encourage a user to save money, complete school or work projects, or the like.

By way of example, a system may receive health goals of a user. The health goals may include general wellness goals, fitness goals, exercise goals, nutrition goals, sleeping goals, or the like or any combination thereof. The health goals may include a schedule, such as a daily schedule, a weekly schedule, a monthly schedule, or the like or any combination thereof. Alternately or additionally, the health goals may include targets, such as a minimum calorie output, a maximum calorie intake, a minimum step count, a minimum exercise time, a target weight, a target body fat percentage, or the like or any combination thereof. The targets may be general targets or may be related to a period in time, such as daily targets, weekly targets, monthly targets, or the like or any combination thereof.

The system may receive data describing a status of the user relative to the identified health goals. The data may be received from personal fitness monitors such as wearable fitness-tracking devices, exercise devices such as treadmills or exercise cycles, wearable computing devices such as smartwatches, personal computing devices such as smartphones, appliances such as refrigerators, or the like or any combination thereof. Alternately or additionally, the data may be received by way of health monitoring systems such as systems related to wearable fitness-tracking devices, systems related to exercise devices, or the like.

The system may compare the status of the user to the health goals of the user. For example, the system may determine whether the user has achieved their health goals, whether the user is likely to achieve their health goals as a matter of course, or the like.

The system may send instructions to environment-altering devices based on the comparison of the status of the user to the health goals of the user. The instructions to the environment-altering devices may be configured to generate an altered environment configured to encourage the user toward achieving their health goals.

The altered environment may physically encourage the user toward achieving their health goals, such as lowering the temperature of the environment to slightly increase a metabolism of the user. Alternately or additionally, the altered environment may withhold something the user may desire until the user makes sufficient progress toward and/or achieves their health goals. For example, the altered environment may block access to entertainment websites, to applications on the user's smartphone, to devices such as televisions and audio systems, or the like or any combination thereof. Alternately or additionally, the altered environment may provide reminders to the user, such as causing the lights in the environment to flash and/or change to a particular color. The reminders may be potentially irritating to the user, such as causing the lights to flash for an extended period of time, continuously playing an audio clip through an audio system at a relatively loud volume, or the like.

The system may send updated instructions to the environment-altering devices based on further comparison of the status of the user to the health goals of the user. The updated instructions may be configured to change the altered environment or to return to an unaltered environment. By way of example, the altered environment may be negated when the status of the user indicates that the user is actively working toward achieving their health goals. Alternately or additionally, the altered environment may be negated when the status of the user indicates that the user has achieved their health goals.

Reference will now be made to the figures wherein like structures will be provided with like reference designations. The drawings are diagrammatic and schematic representations of exemplary embodiments and, accordingly, are not limiting of the scope of the claimed subject matter, nor are the drawings necessarily drawn to scale. The system may include one or more features and/or aspects shown in the drawings, or combinations thereof. The system may also be used in combination with other features and/or aspects depending, for example, upon the intended use of the system.

Figure 1:
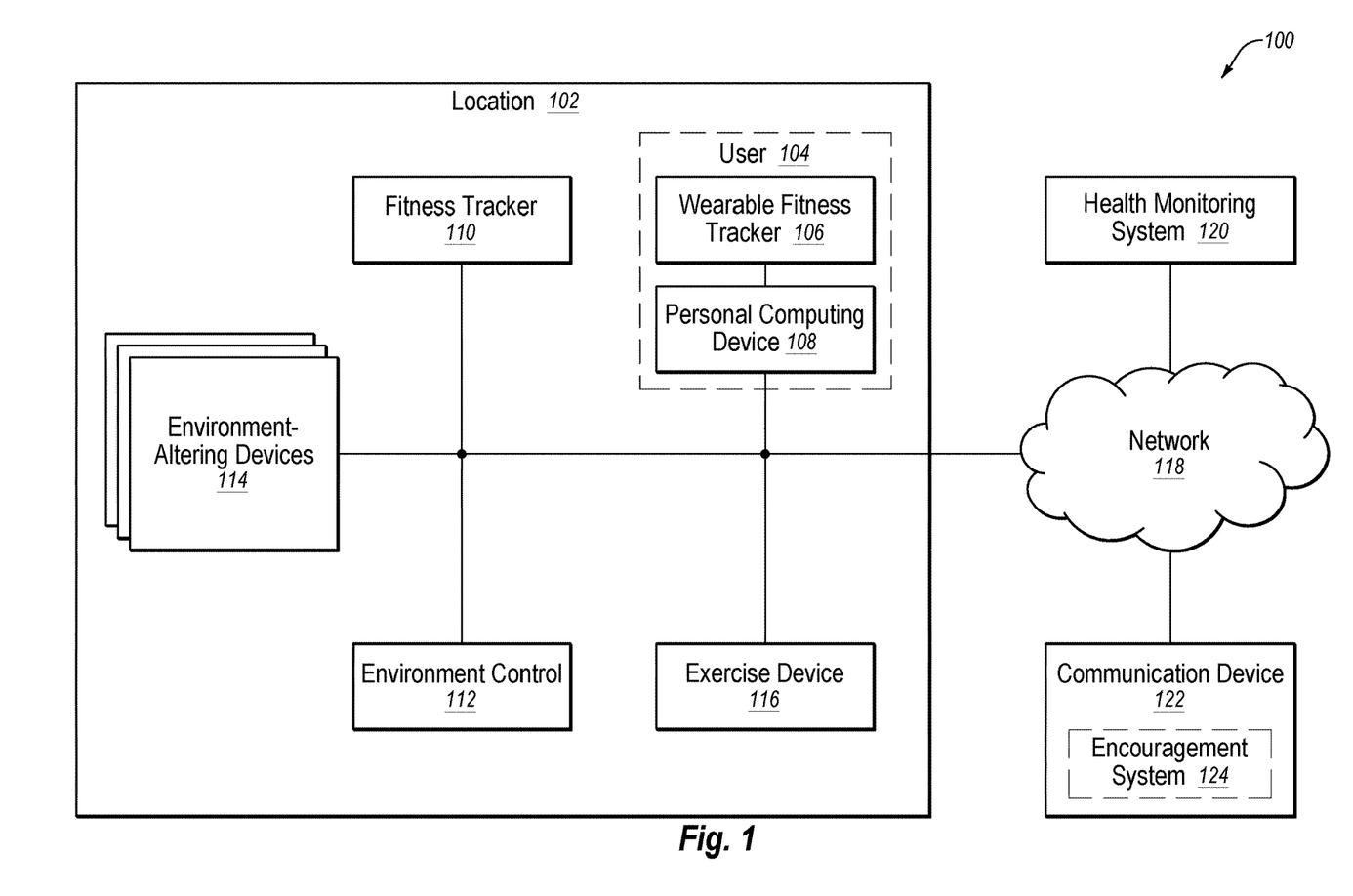
FIG. 1 is a diagram of an example health system.

FIG. 1 is a diagram of an example health system 100. The health system 100 may include a user 104 at a location 102. The user 104 may have a wearable fitness tracker 106 located on the user. The wearable fitness tracker 106 may include sensors for determining activities performed by the user, such as exercising, walking, running, sleeping, sitting, or the like or any combination thereof. Alternately or additionally, the wearable fitness tracker 106 may include sensors for determining physiological conditions of the user 104, such as heart rate, respiration rate, blood pressure, blood glucose level, calorie expenditure, temperature, perspiration, or the like or any combination thereof. In some instances, the wearable fitness tracker 106 may be worn by the user 104 for extended periods. By way of example, the wearable fitness tracker 106 may include a device worn on the user's wrist, upper arm, torso, or the like. Alternately or additionally, the wearable fitness tracker 106 may include a device attached to and/or formed into the user's clothing.

The example health system 100 may include a fitness tracker 110. Like the wearable fitness tracker 106, the fitness tracker 110 may include sensors for determining activities performed by the user 104 and/or physiological conditions of the user 104. By way of example, the fitness tracker 110 may include a scale for determining a weight, body mass index, body fat percentage, or the like or any combination thereof. Alternately or additionally, the fitness tracker 110 may include a motion tracker, sleep tracker, or the like or any combination thereof. In some instances, the fitness tracker 110 may include a device not worn by the user 104 or not worn for extended periods.

The user 104 may have a personal computing device 108 located on or near the user 104. The personal computing device 108 may include a smartphone, smartwatch, tablet computer, or the like. The personal computing device 108 may include sensors for determining data regarding activities performed by the user 104 and/or physiological conditions of the user analogous to the wearable fitness tracker 106 and/or the fitness tracker 110. The personal computing device 108 may access a network 118. The network 118 may include a local area network and/or a wide area network such as the internet.

The health system 100 may include an exercise device 116 located at the location 102. The exercise device 116 may include any form of exercise machine, including treadmills, stationary cycles, Nordic-style skiers, rowers, steppers, hikers, climbers, elliptical or striding devices, or the like.

In some instances, the wearable fitness tracker 106, the personal computing device 108, the fitness tracker 110, and/or the exercise device 116 may communicate with a health monitoring system 120 via the network 118. In some instances, information from the wearable fitness tracker 106 is received by the personal computing device 108 and relayed or otherwise communicated to the health monitoring system 120. Alternately or additionally, exercise devices and/or fitness trackers in other locations (not shown) may communicate with the health monitoring system 120. For example, data from exercise devices used by the user 104 at a fitness center may be communicated to the health monitoring system 120.

The health monitoring system 120 may include a device such as a server accessible over the network 118 via a website, application software, an application programming interface (API), and/or the like for reviewing information collected by the wearable fitness tracker 106, the personal computing device 108, the fitness tracker 110, and/or the exercise device 116. In some instances, the health monitoring system 120 may be offered as a service to purchasers of the wearable fitness tracker 106, the personal computing device 108, the fitness tracker 110, and/or the exercise device 116. Alternately, the health monitoring system 120 may be offered as a separate service that may work with multiple brands of wearable fitness trackers 106, personal computing devices 108, fitness trackers 110, and/or exercise devices 116.

The health system 100 may include a communication device 122 such as a server accessible over the network 118 via a website, application software, an API, and/or the like. The communication device 122 may gather information from the wearable fitness tracker 106, the fitness tracker 110, the personal computing device 108, the exercise device 116, and/or the health monitoring system 120.

In some embodiments, the communication device 122 may include an encouragement system 124. Alternately or additionally, the personal computing device 108, the fitness tracker 110, the exercise device 116, and/or the health monitoring system 120 may include the encouragement system 124. Alternately or additionally, the encouragement system 124 may be included in a standalone device and/or in an optional environment control 112.

In some embodiments, the encouragement system 124 may control environmental parameters of the location 102 via the environment control 112. The environment control 112 may be located within the encouragement system 124, the personal computing device 108, the exercise device 116, or the like. In some embodiments, operation of the environment control 112 may be similar to the environment controller described in U.S. Patent Application Publication No. 2013/0267383, which is incorporated herein by reference in its entirety.

The environment control 112 may communicate with one or more environment-altering devices 114. In some embodiments, the environment control 112 may communicate with the environment-altering devices 114 via the network 118, directly via a wired interface or a wireless interface such as Bluetooth, via the personal computing device 108, or the like or any combination thereof.

The environment-altering devices 114 may include any devices for altering an environment of the location 102. The environment-altering devices 114 may include home-automation devices installed within the location 102, and/or separate devices associated with the location. Environment-altering devices 114 may include heating/cooling systems, humidifiers, dehumidifiers, fans, misters, lighting, electrical switches, electrical sockets, wireless routers, controllable window coverings, audio systems, refrigerators, water heaters, televisions, other appliances, or the like or any combination thereof.

The encouragement system 124 may compare a status of the user 104 to the health goals of the user to determine whether the user 104 has achieved the health goals. The status of the user 104 may be based on data collected by the wearable fitness tracker 106, the personal computing device 108, the fitness tracker 110, the exercise device 116, the health monitoring system 120, and/or the communication device 122.

The status of the user 104 may include data related to activities performed by the user, physiological conditions of the user, or the like. By way of example, the status of the user 104 may include distances the user walked, ran, biked, swam, or the like; amounts of time the user spent performing physically intense activities; an estimated number of calories the user expended and/or consumed; repetitions of particular exercises; or the like or any combination thereof. In some instances, the data may alternately or additionally be based on data reported by the user.

Optionally, the encouragement system 124 may determine whether the user 104 is actively working toward achieving the health goals. For example, the encouragement system 124 may consider the status of the user 104 to determine whether the user 104 is actively using the exercise device 116 or otherwise making progress toward the health goals.

Alternately or additionally, the encouragement system 124 may determine whether the user 104 is projected to achieve the health goals without encouragement. For example, the encouragement system 124 may consider daily habits of the user 104 in projecting activities the user 104 is likely to undertake. In some embodiments, the encouragement system 124 may consider other factors in projecting whether the user 104 is likely to achieve the health goals. For example, the encouragement system 124 may consider the time of day, the day of the week, weather conditions, holidays, a schedule of the user 104, or the like or any combination thereof.

If the user 104 has not achieved the user's health goals, is not actively working toward the achieving the health goals, and/or is not projected to achieve the health goals, the encouragement system 124 may instruct the environment-altering devices 114 to generate an altered environment at the location 102 to encourage the user 104 to achieve the health goals.

By way of example and not of limitation, the encouragement system 124 may instruct a heating/cooling system to lower the temperature of the location 102 to cause the user 104 to physically expend more calories to achieve a calorie consumption goal. For example, the encouragement system 124 may decrease an ambient temperature of the location 102 by instructing a heating system to stop heating the location 102 at a relatively lower temperature. Alternatively, the encouragement system 124 may decrease the ambient temperature of the location 102 by instructing a cooling system to cool the location 102 to the relatively lower temperature. Alternately or additionally, the encouragement system 124 may instruct a router to block access to one or more entertainment websites until the user 104 has achieved a goal of exercising for a particular period of time. Alternately or additionally, the encouragement system 124 may instruct an electrical switch to power down a television or other entertainment device until the health goal is met. Alternately or additionally, the encouragement system 124 may instruct a lighting system to change the color of the lighting of the location 102. Alternately or additionally, the encouragement system 124 may instruct the lighting system to cause the lights to pulse, strobe, or the like. For example, the encouragement system 124 may instruct the lighting system to strobe red light until the user 104 starts working toward the health goal. Alternately or additionally, the encouragement system 124 may instruct a refrigerator to lock its door or a television to display a message instead of functioning normally.

In some embodiments, the encouragement system 124 may monitor the status of the user 104 and may send updated instructions to the environment-altering devices 114. For example, if the user 104 begins actively working toward achieving the health goals, the encouragement system 124 may send updated instructions to negate the altered environment. Alternately, if the user 104 does not begin actively working toward achieving the health goals despite the altered environment, the encouragement system 124 may send updated instructions to escalate the altered environment to further encourage the user 104 to achieve the health goals.

The user 104 may be encouraged to exercise or to otherwise work toward achieving the user's health goals. For example, the altered environment may irritate the user 104 in some manner and the user may work toward the health goals to cease the irritation. For example, the altered environment may include a flashing light and/or an irritating sound that stops when the user 104 begins exercising. Alternately or additionally, the altered environment may eliminate activities that the user 104 may undertake instead of working toward health goals. For example, the altered environment may block access to internet content such as video-streaming internet services, social media websites, or the like that the user 104 may access instead of exercising.

Alternately or additionally, the altered environment may encourage other people (not shown) in the location 102 to also encourage the user 104 to work toward achieving health goals. For example, a family member of the user 104 may ask the user 104 to exercise so that the family member does not have to endure the altered environment.

In some embodiments, the encouragement system 124 may confirm that the user 104 is in the location 102 before altering the environment. For example, the encouragement system 124 may check whether the personal computing device 108 is at the location 102 through global positioning system (GPS) information gathered by the personal computing device 108, by checking to see whether the personal computing device 108 is within range of a router (not shown) at the location, or the like.

In some embodiments, the encouragement system 124 may indicate to the user 104 that a health goal has been met. For example, the encouragement system 124 may instruct the wearable fitness tracker 106, the personal computing device 108, the exercise device 116, the environment-altering devices 114, or the like to display an indicator that the health goal was met. Alternatively or additionally, the encouragement system 124 may invite the user 104 to create a new health goal, update an existing health goal, renew an existing health goal, or the like. Alternately or additionally, the encouragement system 124 may alter the environment of the location 102 to encourage the user 104 to set a new health goal, update an existing health goal, renew an existing health goal, or the like. For example, if the user 104 sets a health goal confined to a particular time period, such as a health goal to exercise for every day for two weeks, the encouragement system 124 may encourage the user 104 to set a new goal after the particular time period has expired. Thus, the encouragement system 124 may encourage the user 104 to continue using the encouragement system 124 and, by extension, to continue to create and achieve health goals.

In some embodiments, the encouragement system 124 may receive override instructions. The override instructions may negate the altered environment and/or otherwise function as if the user 104 has achieved the health goals, described herein as "suspending" the encouragement system 124. In some embodiments, suspending the encouragement system 124 may last for a temporary period of time. For example, the encouragement system 124 may be suspended for a day if the user 104 does not have time to achieve the health goals.

In some embodiments, the override instructions may include a difficult, time consuming, or otherwise unenjoyable task for the user to negate an existing or a soon-to-exist altered environment. For example, the override instructions may include a long, complex code or a series of tasks that have to be performed on the personal computing device 108 if the user 104 wants to suspend the encouragement system 124 on the same day. The user 104 may be further encouraged to work toward achieving health goals when suspending the system requires effort. In some embodiments, the encouragement system 124 may permit the user 104 to easily negate an existing or a soon-to-exist altered environment a particular number of times. For example, the user 104 may be given two "rest days" per week to use as desired.

Alternately or additionally, the encouragement system 124 may be suspended in advance for events or circumstances that may keep the user 104 from exercising. In some embodiments, suspending the encouragement system 124 at a time in the relatively distant future may be uncomplicated, as the user 104 may be expected to make better choices in advance due to hyperbolic discounting. In some embodiments, the encouragement system 124 may require a more unenjoyable task to suspend the encouragement system 124 in the future, particularly if the user 104 appears to be using the feature to needlessly avoid achieving health goals.

In some embodiments, the user 104 may configure the operating parameters of the encouragement system 124. For example, the user 104 may define the altered environment, how and when the encouragement system 124 is to escalate the environment and/or negate the environment, and the like. Influenced by human heuristics and biases, the user 104 may select parameters to generate an altered environment that may be likely to motivate the user 104.

Figure 2:
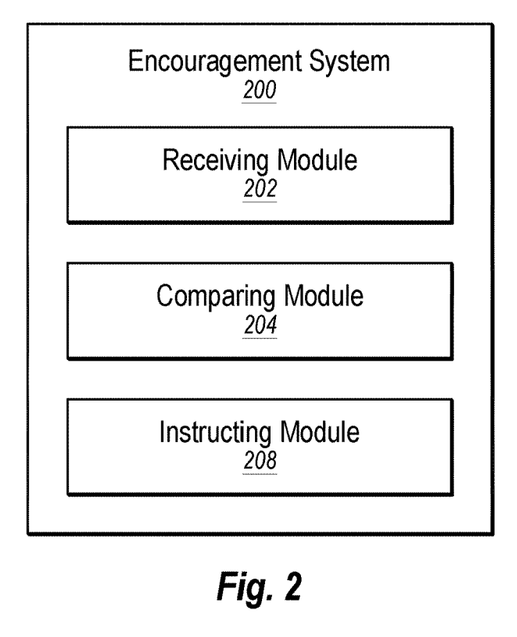
FIG. 2 is a diagram of an example encouragement system that may be employed in the health system of FIG. 1.

FIG. 2 is a diagram of an example encouragement system 200 that may be employed in the health system 100 of FIG. 1. The encouragement system 200 may generally correspond to the encouragement system 124 of FIG. 1.

The encouragement system 200 may include a receiving module 202. The receiving module 202 may receive health goals of a user such as the user 104 of FIG. 1. The health goals may be entered into a website such as a website hosted by the communication device 122 of FIG. 1, into an application installed on a computing device such as the personal computing device 108 of FIG. 1, into a separate device, or the like or any combination thereof.

The health goals may include quantifiable activities to be performed by the user before a deadline or within a particular time period. For example, the health goals may include taking 10,000 steps every day, running for 3 hours every week, sitting for no more than 90 minutes at a time, burning more calories than were consumed for 6 days every week, doing 10 pushups every hour, or the like. In some instances, the health goals may be long-term goals broken down into short-term goals. For example, the health goals may include reducing a body fat percentage of the user by 1% within three months, which may be broken down into weekly goals by the encouragement system 200.

The receiving module 202 may further receive data describing a status of the person. The status may relate to the health goal. For example, the status of the user may include a body composition of the person, a number of steps taken, a distance run, calories consumed, a heart rate, or the like. The receiving module 202 may receive the data from one or more fitness trackers such as the wearable fitness tracker 106 and/or fitness tracker 110 of FIG. 1. Alternately or additionally, the receiving module 202 may receive the data from health monitoring systems and/or communication devices, such as the health monitoring system 120 and/or the communication device 122 of FIG. 1. The receiving module 202 may alternately or additionally receive the data from one or more exercise devices such as the exercise device 116 of FIG. 1. Alternately or additionally, the receiving module 202 may receive data from a computing device such as the personal computing device 108 of FIG. 1.

The receiving module 202 may alternately or additionally receive operating parameters. For example, the receiving module 202 may receive operating parameters from a user via a computing device and/or a communication device, such as the personal computing device 108 and/or the communication device 122 of FIG. 1.

The encouragement system 200 may include a comparing module 204. The comparing module 204 may compare a person's status with the person's health goals to determine whether the user has achieved the health goal, whether the user is projected to achieve the health goals, whether the user is actively working toward achieving the health goals, or the like or any combination thereof. The comparing module 204 may employ machine learning or a similar method for determining whether the user is projected to achieve the health goals and/or is actively working toward achieving the health goals.

The encouragement system 200 may include an instructing module 208. The instructing module 208 may send instructions to environment-altering devices associated with a location of the person, such as the environment-altering devices 114 associated with the location 102 of FIG. 1. In some embodiments, the distribution module 208 may send instructions to the environment altering devices directly, via a network, or the like. In some embodiments, the instructing module 208 may send instructions to the environment-altering devices via an environment control, such as the environment control 112 of FIG. 1. Alternately or additionally, the instructing module 208 may send instructions to the environment-altering devices via another device such as the personal computing device 108, the exercise device 116, and/or the communication device 122 of FIG. 1.

Figure 3:
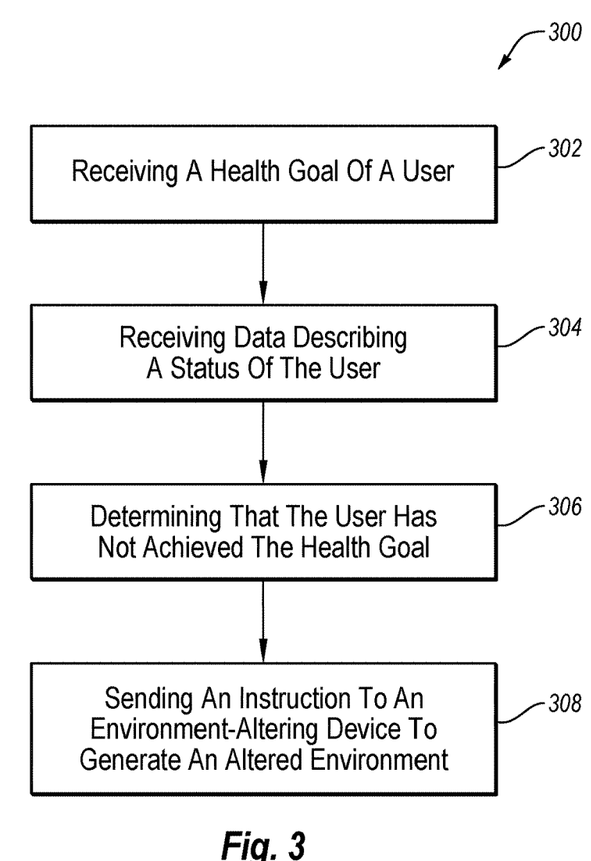
FIG. 3 is a flowchart of an example method that may be performed in the health system of FIG. 1.

FIG. 3 is a flow chart of an example method 300. The method 300 may be performed in the health system 100 of FIG. 1. In some embodiments, the method 300 may be implemented, in whole or in part, by an encouragement system corresponding to the encouragement system 124 of FIG. 1 and/or to the encouragement system 200 of FIG. 2.

The method 300 may begin at block 302, in which a health goal of a user is received. In some embodiments, the health goal of the user may be received in a manner corresponding to reception of the health goals as described with reference to the receiving module 202 of FIG. 2.

In block 304, data describing a status of the user may be received. In some embodiments, the status of the user may be related to the health goal. In some embodiments, the status of the user may be received in a manner corresponding to the reception of a status of the user as described with reference to the receiving module 202.

In block 306, it may be determined that the user has not achieved the health goal. The determination may be based on a comparison of the status of the user and the health goal. In some embodiments, determining that the user has not achieved the health goal may be done in a manner corresponding to comparison of the status of the user and the health goals of the user as described with reference to the comparing module 204 of FIG. 2.

In block 308, an instruction may be sent to an environment-altering device to generate an altered environment. The environment-altering device may be associated with a location of the user. The altered environment may be configured to encourage the user toward achieving the health goal. In some embodiments, sending the instruction to the environment-altering device may correspond to sending instructions to environment-altering devices as described with reference to the distribution module 208 of FIG. 2.

In some embodiments, the altered environment may be associated with a change in a temperature of the location. In some other embodiments, the altered environment may be associated with blocked access to a network location. In yet some other embodiments, the altered environment may be associated with a change in lighting of the location. In still yet some other embodiments, the altered environment may be associated with blocked access to a device located at the location.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

For example, the method 300 may further include receiving data describing an updated status of the user after sending the instruction to the environment-altering device. An updated instruction may be sent to the environment-altering device. The updated instruction may be configured to generate an updated environment.

Alternately or additionally, the method 300 may include determining that the user is actively working toward achieving the health goal. The determination may be based on a comparison of the updated status of the user and the health goal. The updated environment may be configured to negate the altered environment.

The method 300 may alternately or additionally include determining that the user is not actively working toward achieving the health goal. The determination may be based on a comparison of the updated status of the user and the health goal. The updated environment may be configured to further encourage the user toward achieving the health goal.

Alternately or additionally, the method 300 may include determining that the user has achieved the health goal. The determination may be based on a comparison of the updated status of the user and the health goal. The updated environment may be configured to negate the altered environment.

In some embodiments, the method 300 may include determining that the user is not projected to achieve the health goal. The determination may be based on the comparison of the status of the user and the health goal.

The embodiments described herein may physically alter an environment of a location, may instruct an environment-altering device to physically alter the environment of the location, and/or the like. Alternately or additionally, the embodiments described herein may include the use of a special purpose or general-purpose computer including various computer hardware or software modules, as discussed in greater detail below.

Embodiments described herein may be implemented using computer-readable media for carrying or having computer-executable instructions or data structures stored thereon. Such computer-readable media may be any available media that may be accessed by a general purpose or special purpose computer. By way of example, and not limitation, such computer-readable media may include tangible computer-readable storage media including random-access memory (RAM), read-only memory (ROM), electrically erasable programmable read-only memory (EEPROM), compact disc read-only memory (CD-ROM) or other optical disk storage, magnetic disk storage or other magnetic storage devices, or any other storage medium which may be used to carry or store desired program code in the form of computer-executable instructions or data structures and which may be accessed by a general purpose or special purpose computer. Combinations of the above may also be included within the scope of computer-readable media.

Computer-executable instructions include, for example, instructions and data which cause a general purpose computer, special purpose computer, or special purpose processing device to perform a certain function or group of functions. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used herein, the term "module" or "component" may refer to software objects or routines that execute on the computing system. The different components, modules, engines, and services described herein may be implemented as objects or processes that execute on the computing system (e.g., as separate threads). While the system and methods described herein are preferably implemented in software, implementations in hardware or a combination of software and hardware are also possible and contemplated. In this description, a "computing entity" may be any computing system as previously defined herein, or any module or combination of modulates running on a computing system.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method comprising:
    receiving, at a health monitoring system including a server, a health goal of a user;
    receiving, at the health monitoring system from a fitness tracker device, data describing a status of the user, the status of the user related at least in part to the health goal;
    determining, at the health monitoring system, that the user has not achieved the health goal based at least in part on a comparison of the status of the user and the health goal; and sending an instruction from the health monitoring system to a home automation device associated with a location of the user, the instruction configured to instruct the home automation device to generate an altered environment at the location to encourage the user toward achieving the health goal, the altered environment at the location being associated with an adjusted temperature of the location, a blocked access to a network location, a change in lighting of the location, or a blocked access to a device located at the location, or some combination thereof.

2. The method of claim 1, further comprising determining that the user is not projected to achieve the health goal based at least in part on the comparison of the status of the user and the health goal.

3. The method of claim 1, further comprising:
receiving data describing an updated status of the user after sending the instruction to the home automation device; and
sending an updated instruction to the home automation device associated with the location of the user, the updated instruction configured to instruct the home automation device to generate an updated environment at the location.

4. The method of claim 3, further comprising determining that the user is actively working toward achieving the health goal based at least in part on a comparison of the updated status of the user and the health goal, wherein the updated environment is configured to negate the altered environment.

5. The method of claim 3, further comprising determining that the user is not actively working toward achieving the health goal based at least in part on a comparison of the updated status of the user and the health goal, wherein the updated environment is configured to further encourage the user toward achieving the health goal.

6. The method of claim 3, further comprising determining that the user has achieved the health goal based at least in part on a comparison of the updated status of the user and the health goal, wherein the updated environment is configured to negate the altered environment.

7. The method of claim 3, further comprising determining that the user is projected to achieve the health goal based at least in part on a comparison of the updated status of the user and the health goal, wherein the updated environment is configured to negate the altered environment.

8. The method of claim 1, further comprising receiving an operating parameter from the user, wherein the altered environment is further based at least in part on the operating parameter.

9. The method of claim 1, wherein the location of the user is associated with an ambient temperature and the instruction sent to the home automation device is configured to instruct the home automation device to lower the temperature of the location of the user relative to the ambient temperature.

10. The method of claim 1, wherein the altered environment is associated with the blocked access to the network location.

11. The method of claim 1, wherein the altered environment is associated with the change in lighting of the location.

12. The method of claim 1, wherein the altered environment is associated with the blocked access to the device located at the location.

13. One or more tangible computer-readable media storing one or more programs that are configured, when executed, to cause one or more processors to perform a method comprising:
receiving, at a health monitoring system including a server, a health goal of a user;
receiving, at the health monitoring system from a fitness tracker device, data describing a status of the user, the status of the user related at least in part to the health goal;
determining, at the health monitoring system, that the user has not achieved the health goal based at least in part on a comparison of the status of the user and the health goal; and
sending an instruction from the health monitoring system to a home automation device associated with a location of the user, the instruction configured to instruct the home automation device to generate an altered environment at the location to encourage the user toward achieving the health goal, the altered environment at the location being associated with an adjusted temperature of the location, a blocked access to a network location, a change in lighting of the location, or a blocked access to a device located at the location, or some combination thereof.

14. The one or more tangible computer-readable media of claim 13, wherein the method further comprises determining that the user is not projected to achieve the health goal based at least in part on the comparison of the status of the user and the health goal.

15. The one or more tangible computer-readable media of claim 13, wherein the method further comprises:
receiving data describing an updated status of the user after sending the instruction to the home automation device; and
sending an updated instruction to the home automation device associated with the location of the user, the updated instruction configured to instruct the home automation device to generate an updated environment at the location.

16. The one or more tangible computer-readable media of claim 15, wherein the method further comprises determining that the user is actively working toward achieving the health goal based at least in part on a comparison of the updated status of the user and the health goal, wherein the updated environment is configured to negate the altered environment.

17. The one or more tangible computer-readable media of claim 15, wherein the method further comprises determining that the user is not actively working toward achieving the health goal based at least in part on a comparison of the updated status of the user and the health goal, wherein the updated environment is configured to further encourage the user toward achieving the health goal.

18. The one or more tangible computer-readable media of claim 15, wherein the method further comprises determining that the user has achieved the health goal based at least in part on a comparison of the updated status of the user and the health goal, wherein the updated environment is configured to negate the altered environment.

19. The one or more tangible computer-readable media of claim 15, wherein the method further comprises determining that the user is projected to achieve the health goal based at least in part on a comparison of the updated status of the user and the health goal, wherein the updated environment is configured to negate the altered environment.

20. The one or more tangible computer-readable media of claim 13, wherein the altered environment is associated with at least one of: a change in a temperature of the location, a blocked access to a network location, a change in lighting of the location, and blocked access to a device located at the location.

\* \* \* \* \*